United States Patent [19]

Sato et al.

[11] Patent Number: 5,481,049

[45] Date of Patent: Jan. 2, 1996

[54] PROCESS FOR PRODUCING ALKADIENOLS

[75] Inventors: Keiichi Sato; Yoko Seto, both of Tokyo; Iwao Nakajima, Yokohama, all of Japan

[73] Assignee: Mitsubishi Chemical Corporation, Japan

[21] Appl. No.: 216,106

[22] Filed: Mar. 22, 1994

[30] Foreign Application Priority Data

Mar. 30, 1993 [JP] Japan ................................. 5-072045

[51] Int. Cl.$^6$ ............................ C07C 29/36; C07C 33/02
[52] U.S. Cl. ........................................ 568/909.5; 568/845
[58] Field of Search ................................. 568/909.5, 845

[56] References Cited

U.S. PATENT DOCUMENTS

| | | |
|---|---|---|
| 553,584 | 1/1896 | Huff et al. . |
| 3,670,032 | 6/1972 | Romanelli ............................... 568/903 |
| 4,962,243 | 10/1990 | Roeper et al. ....................... 568/909.5 |
| 5,057,631 | 10/1991 | Tokitoh et al. ....................... 568/909.5 |
| 5,169,981 | 12/1992 | Packett ................................. 568/909.5 |
| 5,302,750 | 4/1994 | Livingston ............................ 568/909.5 |

FOREIGN PATENT DOCUMENTS

| | | |
|---|---|---|
| 0287066 | 10/1988 | European Pat. Off. . |
| 0361304 | 4/1990 | European Pat. Off. . |
| 3112213 | 1/1982 | Germany . |
| 3925217 | 1/1991 | Germany . |
| 4233235 | 2/1994 | Germany . |

*Primary Examiner*—Joseph E. Evans
*Attorney, Agent, or Firm*—Nixon & Vanderhye

[57] ABSTRACT

The disclosure is a process for producing an alkadienol, which comprises reacting a conjugated alkadiene and water in the presence of carbon dioxide using a palladium compound and a phosphine compound as catalyst, the reaction being carried out with a free phosphine compound present in the reaction solution.

20 Claims, No Drawings

PROCESS FOR PRODUCING ALKADIENOLS

BACKGROUND OF THE INVENTION

The present invention relates to a process for producing alkadienols. More particularly, it relates to a process for producing alkadienols which are dimerized hydrates of conjugated alkadienes, comprising reacting conjugated alkadienes with water in the presence of carbon dioxide using a palladium compound and a phosphine compound as catalyst.

Alkadienols, especially octadienols such as octa-2,7-diene-1-ol are important compounds in chemical industries as an intermediate for the production of n-octanol, its esters and the like. As the process for producing such alkadienols, a process comprising reacting conjugated alkadienes and water in the presence of carbon dioxide using a palladium compound and a phosphine compound as catalyst is known from, for instance, Chemical Communications. 330 (1971), and Japanese Patent Publication (KOKOKU) No. 50-10565. It is also known that triphenylphosphine is preferred as the phosphine compound used as ligand of the palladium compound, but even in this case, the yield of alkadienols and the selectivity for the desired octa-2,7-diene-1-ol are still unsatisfactory. It is further known from the above-mentioned Chemical Communications, that when triphenylphosphine is used in an amount of more than about 6 times by mole of palladium, the yield of alkadienols is decreased. Thus, there is a problem that this method was subject to restrictions on its operating conditions.

In Japanese Patent Application Laid-Open (KOKAI) No. 64-85988, there is described that as catalyst of the reaction, a low-valency palladium complex containing a ligand such as tri-substituted phosphine or a chemical species prepared by reducing a palladium (II) compound in the presence of a ligand such as trisubstituted phosphine is used. As one of the problems of the telomerization reaction using a palladium catalyst, there is described that in case the telomerization reaction is carried out by using a trisubstituted phosphine in excess of palladium, a long induction period is required for the reaction even when a low-valency palladium complex which is assumed as a catalytic activation species and prepared by using a palladium compound and a trisubstituted phosphine, is used as catalyst for the telomerization reaction. According to Japanese Patent Application Laid-Open (KOKAI) No. 64-85988, it is disclosed that the above reaction proceeds without a long induction period when the reaction is carried out in the presence of a telomerization catalyst composed of a palladium compound and a phosphonium salt which has been transformed into a specified structure as a phosphorous compound. Thus, the Japanese Patent Application Laid-Open (KOKAI) No. 64-85988 suggests that even if a phosphine compound is added to the reaction system as a catalyst component, it is transformed in the reaction system and exists as a phosphonium salt during and at the completion of the reaction.

It has been known to use a palladium compound and a phosphine compound as catalyst of the above-mentioned reaction, but full investigations have not been made on the form of the catalyst in the reaction solution.

In a complex catalytic reaction, the metallic component of the catalyst plays an important role, but the selection of the kind of the ligand used and the reaction conditions is also closely connected with the catalytic reaction activity and selectivity, and even when using a catalyst which has been popularly used in the art, the desired reaction result may not be obtained depending on the form of the catalyst in the reaction solution.

The present inventors have made extensive researches for providing an industrially advantageous process for the preparation of alkadienols, which is capable of producing a desired alkadienol in a high yield and with high selectivity from a dimerization hydration reaction which comprises reacting a conjugated alkadiene and water in the presence of carbon dioxide by using a palladium compound and a phosphine compound as catalyst, and as a result, have found that quite surprisingly a desired alkadienol, specifically octa-2,7-diene-1-ol in case of using 1,3-butadiene as conjugated alkadiene, can be obtained in a high yield and with high selectivity even at a low palladium concentration when a phosphine compound used as a catalyst component is allowed to exist in the reaction system not in the form of a phosphonium salt or phosphine oxide in the conventional reaction solution but in the form of a free phosphine compound. The present invention has been attained on the basis of this finding.

SUMMARY OF THE INVENTION

The object of the present invention is to provide an industrial process for producing alkadienols in a high yield and with high selectivity from a dimerization hydration reaction, which comprises reacting a conjugated alkadiene and water in the presence of carbon dioxide by using a palladium compound and a phosphine compound as catalyst.

To accomplish the aim, in an aspect of the present invention, there is provided a process for producing alkadienols, which comprises reacting a conjugated alkadiene and water in the presence of carbon dioxide using a palladium compound and a phosphine compound as catalyst, the reaction being carried out with a free phosphine compound present in the reaction solution.

DETAILED DESCRIPTION OF THE INVENTION

The feature of the present invention lies in carrying out the reaction with a free phosphine compound present in the reaction solution.

"To carry out the reaction with a free phosphine compound present in the reaction solution" in the present invention means to carry out the reaction in a state where a free phosphine compound exists in the reaction solution not only in the initial stage of the reaction but also through the period when the reaction is in progress. This means that a free phosphine compound is allowed to exist in the reaction solution even in a state where the reaction has proceeded to a stage at which the product alkadienol exists in an amount of not less than 100 moles, preferably not less than 1,000 moles based on one mole of palladium, or in an amount of not less than 10 moles, preferably not less than 100 moles based on one mole of phosphorus. In the present invention, it is especially preferable that a free phosphine compound exists in the reaction solution from the initial stage till the completion of the reaction.

The "free phosphine compound present in the reaction solution" in the present invention is not a phosphine compound forming a ligand of palladium and a phosphonium salt, and is a phosphine compound which is distinguished therefrom and exists in a free state. Such free phosphine compound is also defined by the fact that the shift value shown when phosphorus-NMR of the reaction solution was measured at ordinary temperature under ordinary pressure immediately after sampling of the reaction solution in the course of the reaction or immediately after the completion of the reaction is equal to the shift value shown when the same measurement was conducted by using a solution obtained by dissolving the phosphine compound in a solvent of the same composition as the reaction solution without containing the transition metal elements such as palladium. The amount of the free phosphine compound in the reaction solution is not specified, but it is preferable that the amount of the free phosphine compound is 0.3 to 250 moles, preferably 1 to 150 moles, more preferably 1.5 to 100 moles based on one mole of palladium. By so controlling the amount of the said free phosphine compound, it is possible to carry out the reaction in a favorable way even at a low palladium concentration. Especially the catalytic activity of palladium is high when the amount of the free phosphine compound is 2 to 100 moles based on one mole of palladium. The whole amount of the phosphine compound used may exist in the form of a free phosphine compound in the reaction solution.

In the present invention, the conditions under which a free phosphine compound is allowed to exist in the reaction solution are not specified as far as the reaction is carried out with a free phosphine compound present in the reaction solution. In the present invention, however, among the various factors mentioned below, especially the kind of the phosphine compound used, the ratio of phosphine compound to palladium and the reaction temperature are important factors so as to allow a free phosphine compound to exist in the reaction solution. By properly selecting these factors and carrying out a dimerization hydration reaction with a free phosphine compound present in the reaction system, the catalyst components are utilized at high efficiency, the selectivity for alkadienols is improved, and consequently the very excellent reaction results (high yield and high selectivity) can be obtained even at a low palladium concentration.

As the conjugated alkadienes usable for preparation of alkadienols, which is reacted with water in the process of the present invention, 1,3-butadiene, 2-ethyl-1, 3-butadiene, 2,3-dimethyl-1,3-butadiene, isoprene, 1,3-pentadiene, chloroprene and 1,3-octadiene may be exemplified. In the case of 1,3-butadiene, usually refined 1,3-butadiene and BBP (butane-butadiene product) such as a $C_4$ fraction mixture in the naphtha cracking product are used as they are easily available.

In case of using BBP as starting material for the economical reason, it is preferable to remove acetylenes and allenes contained in BBP. Known methods can be used for removing or reducing acetylenes and allenes from BBP. It is preferable that the total concentration of acetylenes and allenes in the starting 1,3-butadiene to be subjected to the dimerization hydration reaction for preparation of octadienols after removal or reduction of the acetylenes and allenes, is as low as possible, but it is preferably not more than 1.0 wt % based on 1,3-butadiene.

As water used as another reactant, water having purity of a degree which gives no adverse effect to the dimerization hydration reaction is appropriately used. The amount of water used is not specified, but preferably it is selected from the range of 0.5 to 10 moles, more preferably 1 to 5 moles based on one mole of conjugated alkadiene.

In the present invention, a palladium compound is used as main catalyst component. The form and valency of the palladium compound used in the present invention are not necessarily specified. The palladium compounds usable in present invention are those having as ligand a phosphine compound used as co-catalyst, for example, 0-valent palladium complexes such as bis(phosphine)palladium (0), tris(phosphine)palladium (0), tetrakis(phosphine)palladium (0), tetrakis(triphenylphosphine) palladium (0), tris(dibenzylideneacetone)dipalladium (0) and (1,5-cycloalkadiene) (maleic anhydride) palladium (0); palladium inorganic salts such as palladium nitrate; palladium organic salts such as palladium acetate; and divalent palladium complexes such as bis (acetylacetone)palladium (II) and bis (tributylphosphine) palladium (II) acetate.

The amount of the palladium compound used is variable, but preferably it is selected within the range of 0.000002 to 1 moles, more preferably 0.00002 to 0.1 moles (calculated as palladium) based on one mole of conjugated alkadiene. According to the process of the present invention, since the catalyst components in the reaction solution can be utilized efficiently owing to the presence of a free phosphine compound in the reaction solution, it is possible to carry out the reaction in a favorable way even at a very low palladium concentration in the range of 0.00002 to 0.0015 moles, further 0.00002 to 0.0006 moles (calculated as palladium) based on one mole of conjugated alkadiene.

As the phosphine compounds usable as co-catalyst in the present invention, known trialkylphosphines, dialkylmonoarylphosphines, monoalkyldiarylphosphines and triarylphosphines may be exemplified. Of these compounds, monoalkyldiarylphosphines and triarylphosphines are preferred. In the present invention, it is a feature to carry out the reaction with a free phosphine compound present in the reaction solution. In view of this, among the said compounds, it is preferable to use a triarylphosphine compound having at least one aryl group having a substituent at the ortho-position. The especially preferred phosphine compounds for use in the present invention are those represented by the following formula (I):

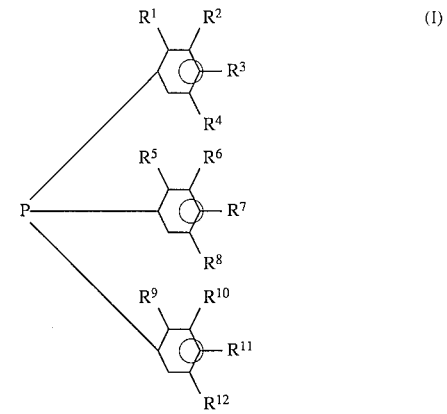

wherein $R^1$, $R^5$ and $R^9$ represent independently a hydrogen or a hydrocarbon group; and $R^2$, $R^3$, $R^4$, $R^6$, $R^7$, $R^8$, $R^{10}$, $R^{11}$ and $R^{12}$ represent independently a hydrogen, an electron donative group or an electron attactive group, but $R^1$, $R^5$ and $R^9$ is not hydrogen, simultaneously.

As examples of the hydrocarbon groups represented by $R^1$, $R^5$ and $R^9$ in the above formula (I), $(C_1-C_{10})$alkyl, $(C_6-C_{20})$aryl and $(C_1-C_{10})$alkoxy can be exemplified. It is preferred that $R^1$, $R^5$ and $R^9$ in the above formula (I) are $(C_1-C_6)$alkyl, $(C_6-C_{10})$aryl and $(C_1-C_6)$alkoxy. As examples of the electron donative groups represented by $R^2$ $R^3$ $R^4$ $R^6$ $R^7$, $R^8$, $R^{10}$, $R^{11}$ and $R^{12}$, $(C_1-C_{20})$alkyl, $(C_1-C_{20})$alkylamino, $(C_1-C_{20})$alkoxy, sulfo$(C_1-C_{20})$alkyl and salts thereof, amino groups and $(C_1-C_{20})$alkyl-substituted amino can be exemplified. It is preferred that the electron donative groups represented by $R^2$ $R^3$ $R^4$ $R^6$ $R^7$, $R^8$, $R^{10}$, $R^{11}$ and $R^{12}$ are $(C_1-C_{10})$alkyl, $(C_1-C_{10})$alkylamino, $(C_1-C_{10})$alkoxy, sulfo$(C_1-C_{10})$alkyl and salts thereof, amino groups and $(C_1-C_{10})$alkyl-substituted amino. As examples of electron attractive groups, sulfo and salts thereof can be exemplified.

As the compounds represented by the formula (I), hydrophobic phosphine compounds such as tri(o-methylphenyl)phosphine, di(o-methylphenyl)phenylphosphine, (o-methylphenyl)diphenylphosphine, tri(o-ethylphenyl)phosphine, di(o-ethylphenyl)phenylphosphine, (o-ethylphenyl)di(phenyl)phosphine, tri(o-propylphenyl)phosphine, tri(o-butylphenyl)phosphine, tri(o-biphenylyl)phosphine, tri(2,6-dimethylphenyl)phosphine, tri(2,5-dimethylphenyl)phosphine, tri(2,4-dimethylphenyl)phosphine, tri(2,3-dimethylphenyl)phosphine, tri(2,4,6-trimethylphenyl)phosphine, tri (2,4,5trimethylphenyl)phosphine, tri (2,3,4-trimethylphenyl)phosphine, tri (2,3,4,5-tetramethylphenyl)phosphine, tri (2,5-diethylphenyl)phosphine, tri (2,4-diethylphenyl) phosphine, tri (2,5-dipropylphenyl)phosphine, tri(2,4-dipropylphenyl)phosphine, tri (2,5-dibutylphenyl)phosphine, tri (2,4-dibutylphenyl)phosphine, tri(2-methyl-4-octylphenyl)phosphine, tri (2-methyl-5-octylphenyl)phosphine, tri (2-methyl-4-methoxyphenyl)phosphine, tri (2-methyl-5-methoxyphenyl)phosphine, tri (2-methyl-4-octoxyphenyl)phosphine, and tri (2-methyl-5-octoxyphenyl)phosphine; and hydrophilic phosphine compounds such as tri(2-methyl-4-(2'-sodium sulfonate ethyl)phenyl)phosphine, tri(2-methyl-5-(2'-sodium sulfonate ethyl)phenyl)phosphine, tri(2-methyl-4-(2'-lithium sulfonate ethyl)phenyl)phosphine, tri(2-methyl-5-(2'-lithium sulfonate ethyl)phenyl)phosphine, tri(2-methyl-5-sodium sulfonate phenyl)phosphine, tri(2-methyl-5-lithium sulfonate phenyl)phosphine, and tri(2-methyl-4-N,N-dimethytaminophenyl)phosphine may be exemplified.

Of the electron donative groups, $(C_1-C_4)$alkyl and $(C_1-C_4)$alkoxy are preferred.

In view of synthesis of phosphine compound, it is preferred to select the compounds represented by the formula (I), wherein $R^1$, $R^5$ and $R^9$ are the same group and represent a $(C_1-C_4)$alkyl; $R^2$, $R^6$ and $R^{10}$ are the same and represent a hydrogen, a $(C_1-C_4)$alkyl, a $(C_1-C_4)$alkoxy, a sulfo or a salt thereof, or a sulfo$(C_1-C_4)$alkyl or a salt thereof; $R^3$, $R^7$ and $R^{11}$ are the same and represent a hydrogen, a $(C_1-C_4)$alkyl, a $(C_1-C_4)$alkoxy, a sulfo or a salt thereof, or a sulfo$(C_1-C_4)$alkyl or a salt thereof; and $R^4$, $R^8$ and $R^{12}$ are the same and represent a hydrogen, a $(C_1-C_4)$alkyl, a $(C_1-C_4)$alkoxy, a sulfo or a salt thereof, or a sulfo$(C_1-C_4)$alkyl or a salt thereof.

Tolman's cone angle (Chem. Rev., 77, 313, 1977) is referred to as an index for indicating steric bulkiness of a ligand. According to this index, the cone angle of tri(o-methylphenyl)phosphine is 194°. When the cone angle is measured from the structure calculated by MOPAC (Ver. 6AM1) (semi-empirical molecular orbital calculation program), the corn angle of tri(o-methylphenyl)phosphine is given as 210°.

Of the phosphine compounds mentioned above, those whose cone angle calculated by MOPAC is not less than 200°, preferably 200° to 270°, are favorably used in the present invention as they give rise to a good result of reaction.

The phosphine compounds which give rise to a favorable cone angle, may include those represented by the following structural formulae:

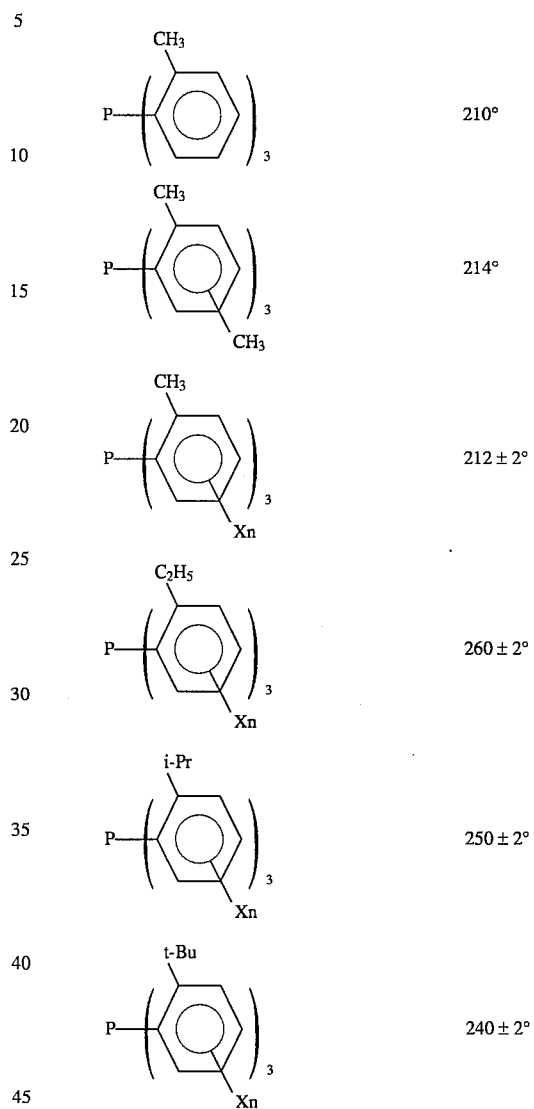

In the above formulae, X represents a $(C_1-C_{10})$alkyl, a $(C_1-C_{10})$alkoxy, a sulfo or a salt thereof, a sulfo$(C_1-C_{10})$alkyl or a salt thereof, an amino or a $(C_1-C_{10})$alkyl-substituted amino; n is an integer of 0 to 3, and when n=2 or 3, each X may be the same or different from each other.

Alkali metal salts such as lithium salt and sodium salt can be cited as typical examples of the salts of sulfo or sulfoalkyl.

In the case of tri(substituted phenyl)phosphine, the cone angle is substantially decided by bulkiness of the substituent at the ortho-position and is little affected by the kind of the substituent at the meta- or para-position. Therefore, the cone angle of tri(substituted phenyl)phosphine having a $(C_1-C_4)$alkyl group at the ortho-position as the above-shown compounds is about 200° to 270°.

As the free phosphine compound in the present invention, since the phosphine compound used as a co-catalyst exists as a free state thereof in the reaction solution, the above-mentioned phosphine compounds can be cited.

In the present invention, the reaction needs to be carried out with a free phosphine compound present in the reaction solution, and the amount of phosphine compound mentioned above to be used is selected from the range of 0.1 to 250 moles, preferably 3 to 150 moles, more preferably 5 to 150 moles, still more preferably 10 to 100 moles based on one mole of palladium. It is especially preferred that the amount of the free phosphine compound is 25 to 100 moles based on one mole of palladium in terms of yield of the product alkadienol and activity of the catalyst palladium. It is preferable that the amount of the phosphine compound used is within ranges where the said compound can be dissolved in the reaction solution under the specified reaction conditions in the above-defined range. The reaction may be carried out while supplying the phosphine compound within ranges where the compound is dissolved in the reaction solution, for the purpose of allowing a free phosphine compound to exist consistently in the reaction solution.

In the process of the present invention, the reaction of a conjugated alkadiene and water is carried out in the presence of a palladium compound such as mentioned above, a free phosphine compound such as exemplified above and carbon dioxide. Carbon dioxide used in the present invention may be supplied in any form as far as carbon dioxide exists in the reaction solution. For instance, it may be supplied in the form of molecular carbon dioxide, carbonic acid, carbonate, bicarbonate or an addition product of carbonic acid and an amine. The upper limit of the amount of carbon dioxide used is defined by the economical reason, and the reaction is not affected even if carbon dioxide is applied in an excess amount. Usually, however, carbon dioxide is used in an amount of not less than one mole, preferably not less than 10 moles based on one mole of palladium.

In carrying out the reaction of a conjugated alkadiene and water, it is preferred to use a solvent for smooth progress of the reaction. As the solvents usable for this purpose, ethers such as diethyl ether, dioxane, tetrahydrofuran, ethylene glycol dimethyl ether and tetraethylene glycol dimethyl ether; ketones such as acetone, methyl ethyl ketone, diethyl ketone, methyl isopropyl ketone and ethyl n-butyl ketone; nitriles such as acetonitrile, propionitrile and benzonitrile; aromatic hydrocarbons such as benzene, toluene, xylene and ethylbenzene; alkanes such as pentane, hexane and heptane; alkenes such as hexene and octene; sulfoxides such as dimethyl sulfoxide; sulfones such as sulforan; nitro compounds such as nitrobenzene and nitromethane; pyridine and its derivatives such as a-picoline; amines such as triethylamine; amides such as acetamide, propionamide, N,N-dimethylformamide, N,N-dimethylacetamide and N,N-diethylacetamide; alcohols such as methanol, ethanol, n-propanol, isopropanol, n-butanol, isobutanol, t-butanol and n-alkanol; and carboxylic acids such as formic acid, acetic acid, propionic acid and butyric acid may be exemplified. These solvents may be used either singly or as a mixture. It is to be noted, however, that in case of using a lower alcohol, there are formed by-products such as alkoxyalkadiene, and in case of using a lower carboxylic acid, there are formed by-products such as acylalkadiene, thereby complicating the reaction system.

Among the solvents, ethers, ketones, alkanes, alkenes, sulfones, amines and amides are preferred.

The amount of the solvent used is not specified, but it is usually selected from the range of 0.1 to 50 parts by weight, preferably 1 to 10 parts by weight based on one part by weight of conjugated alkadiene.

The reaction temperature for reacting a conjugated alkadiene and water may be selected from the range of room temperature to around 180° C., but preferably it is selected from the range of around 50° to 130° C., more preferably 75° to 110° C., still more preferably 85° to 100° C.

The reaction pressure may be selected from the range of ordinary pressure to around 200 kg/cm$^2$. A gas inert to the reaction, such as nitrogen, helium or argon, may be allowed to coexist, beside carbon dioxide, in the reaction system.

The process of the present invention may be carried out according to a known reaction mode such as continuous, semi-continuous or batchwise, but in industrial operation, it is advantageous in terms of economy to carry out the process in continuous.

In the present invention, a conjugated alkadiene and water are reacted under the above-described reaction conditions to produce an alkadienol. In the reaction solution produced by this reaction (which is called "produced solution" hereinafter), there are contained the catalyst, an alkadienol which is the objective reaction product, the by-products such as alkatrienes, dialkadienyl ethers, organic carboxylic acids and esters, solvent, unreacted conjugated alkadiene and water. In case of using 1,3-butadiene as the starting conjugated alkadiene, the produced alkadienols are octadienlos and octa-2,7-diene-1-ol is produced as the principal reaction product, while octa-1,7-diene-3-ol, octatrienes, dioctadienyl ethers, organic carboxylic acids and esters are yielded as by-products. The yield of the by-products depends on the reaction conditions, but it is usually around a few molar percents based on the conjugated alkadiene. After the reaction, alkadienol can be recovered by known means such as distillation separation or extraction separation.

The produced solution or the solution containing the catalyst components after separation of alkadienol from the produced solution may be at least partly recycled into the reaction solution for the hydration dimerization reaction. The catalyst-containing solution may be subjected to a treatment for separating the high-boiling point by-products prior to recycling. The phosphorus compounds other than the free phosphine compound, which have been formed after transformation in the reaction solution and are contained in the produced solution, may be decomposed into a free phosphine compound by subjecting the produced solution either immediately to a heat-treatment, a contacting-treatment with hydrogen gas or a contacting-treatment with a basic material such as sodium hydroxide, or after separating the starting compounds, alkadienol and solvent from the said produced solution to a heat-treatment, a contacting-treatment with hydrogen gas or a contacting-treatment with a basic material such as sodium hydroxide, and the decomposition product may be recycled into the reaction solution for the hydration dimerization reaction.

According to the process of the present invention, when an alkadienol is produced by reacting a conjugated alkadiene and water in the presence of carbon dioxide using a palladium compound and a phosphine compound as catalyst, the catalyst components are effectively and efficiently utilized even at a low palladium concentration, and a desired alkadienol can be produced in a high yield and with high selectivity by allowing a free phosphine compound to exist in the reaction system. Thus, the present invention offers a great benefit to the industries.

EXAMPLES

The present invention is described in further detail below with reference to the examples, which examples however are intended to be illustrative rather than restrictive of the scope of the invention.

In the Tables given below, the following abbreviations are used.

Pd/BD: Ratio of the number of moles of the supplied palladium compound to the number of moles of the supplied butadiene.

Phosphine/Pd: Ratio of the number of moles of the supplied phosphine compound to the number of moles of the supplied palladium compound.

ΣHOD yield: Yield (%) of the produced octadienol based on the supplied butadiene.

1-HOD/ΣHOD: Ratio (%) of octa-2,7-diene-1-ol (1-HOD) in the produced octadienols.

ΣHOD selectivity: Selectivity (%) of the produced octadienols against the reacted butadiene.

Free P/Pd: Ratio of the number of moles of the free phosphine compound measured by P-NMR to the number of moles of the supplied palladium compound.

TOF: The number of moles of butadiene converted to octadienols based on one mole of palladium per hour.

Example 1

Into a stainless steel-made 200 ml autoclave, 0.063 mmol of palladium acetate, 1.0 mmol of tri(2,4-dimethylphenyl)phosphine, 47 ml of acetone and 6.7 ml of water were supplied under a nitrogen gas atmosphere, followed by introduction of 13.8 g of 1,3-butadiene and 8 g of carbon dioxide. The resultant mixture was heated with stirring at 800 r.p.m. until the internal temperature became 75° C. requiring 20 minutes After the reaction at a temperature of 75° C. for 4 hours, the reaction solution was analyzed by gas chromatography and P-NMR. The results are shown in Table 1.

Example 2

The same procedure as Example 1 was conducted except that the amount of tri(2,4-dimethylphenyl)phosphine was changed to 3.0 mmol. The results are shown in Table 1.

Comparative Example 1

The same procedure as Example 1 was conducted except that the amount of tri(2,4-dimethylphenyl)phosphine was changed to 0.2 mmol. The results are shown in Table 1.

Example 3

The same procedure as Example 1 was conducted except that the amount of tri(2,4-dimethylphenyl)phosphine was changed to 2.0 mmol and that the reaction temperature was changed to 90° C. The results are shown in Table 1.

The reaction conditions are also shown in Table 1.

TABLE 1(I)

| | Reaction Conditions | | | |
|---|---|---|---|---|
| | Pd/BD | Phosphine/Pd | Reaction temp. (°C.) | Reaction time (hr) |
| Example 1 | $2.47 \times 10^{-4}$ | 16 | 75 | 4 |
| Example 2 | " | 48 | " | " |
| Comp. Example 1 | " | 3.2 | " | " |
| Example 3 | " | 32 | 90 | " |

| | Reaction Results | | | | |
|---|---|---|---|---|---|
| | Free P/Pd | ΣHOD yield (%) | 1-HOD/ΣHOD (%) | ΣHOD selectivity (%) | TOF |
| Ex. 1 | 2.73 | 50.8 | 96.3 | 89.5 | 514 |
| Ex. 2 | 11.3 | 52.0 | 96.1 | 89.6 | 564 |
| Comp. Ex. 1 | 0 | 27.2 | 95.9 | 89.5 | 293 |
| Ex. 3 | 17.6 | 67.1 | 94.6 | 92.6 | 696 |

Example 4

The same procedure as Example 1 was conducted except that the amount of palladium acetate was changed to 0.50 mmol and that 2.0 mmol of tri(o-methylphenyl)phosphine was used in place of 1.0 mmol of tri(2,4dimethylphenyl)phosphine. The results are shown in Table 2.

Examples 5–9 and Comparative Example 2

The same procedure as Example 1 was carried out except that 2.0 mmol of the phosphine compounds shown in Table 2 were used in place of tri(2,4-dimethylphenyl)phosphine, and that the reaction temperature was changed to 90° C. The results are shown in Table 2.

The reaction conditions are also shown in Table 2.

Example 10 and Comparative Example 3

The same procedure as Example 1 was conducted except that the amounts of palladium acetate and 1,3-butadiene were changed to 0.2 mmol and 25.6 g. respectively, that 2.4 mmol of di(o-methylphenyl)-(2-methyl-5-sodium sulfonate phenyl)phosphine (Example 10) or diphenyl(5-sodium sulfonate phenyl)phosphine (Comparative Example 3) was used in place of tri(2,4-dimethyl)phosphine, that 60 ml of sulforan containing 45 wt% of water and 11 ml of triethylamine were used as solvent in place of acetone and water, and that the reaction was carried out at a temperature of 85° C. for 2 hours. The results are shown in Table 3.

The reaction conditions are also shown in Table 3.

TABLE 2(I)

| | Reaction Conditions | | | |
|---|---|---|---|---|
| | Phosphine compound | Pd/BD | Phosphine/Pd | Reaction temp. (°C.) | Reaction time (hr) |
| Ex. 4 | Tri(o-methylphenyl)phosphine | $1.96 \times 10^{-3}$ | 4 | 75 | 4 |
| Ex. 5 | Tri(o-methylphenyl)phosphine | $2.47 \times 10^{-4}$ | 32 | 90 | " |
| Ex. 6 | Tri(2,5-dimethylphenyl)phosphine | " | " | " | " |
| Ex. 7 | Tri(2-methyl-4-methoxyphenyl)phosphine | " | " | " | " |
| Ex. 8 | Tri(2-ethylphenyl)phosphine | " | " | " | " |
| Ex. 9 | Di(2-ethylphenyl)phenylphosphine | " | " | " | " |

TABLE 2(I)-continued

| | | " | " | " | " |
|---|---|---|---|---|---|
| Comp. Ex. 2 | Triphenyl-phosphine | | | | |

| | Reaction Results | | | | |
|---|---|---|---|---|---|
| | Free P/Pd | ΣHOD yield (%) | 1-HOD/ΣHOD (%) | ΣHOD selectivity (%) | TOF |
| Ex. 4 | 1.70 | 79.3 | 92.7 | 95.1 | 99 |
| Ex. 5 | 28.6 | 79.3 | 94.3 | 92.5 | 798 |
| Ex. 6 | 24.4 | 77.6 | 94.6 | 93.5 | 783 |
| Ex. 7 | 4.06 | 56.4 | 95.2 | 90.5 | 570 |
| Ex. 8 | 30.5 | 68.3 | 93.2 | 89.8 | 701 |
| Ex. 9 | 12.1 | 64.0 | 91.6 | 89.4 | 640 |
| Comp. Ex. 2 | 0 | 27.5 | 73.9 | 69.0 | 285 |

TABLE 3(I)

| | Reaction Conditions | | | | |
|---|---|---|---|---|---|
| | Phosphine compound | Pd/BD | Phosphine/Pd | Reaction temp. (°C.) | Reaction time (hr) |
| Ex. 10 | Di(o-methylphenyl)-(2-methyl-5-sodium sulfonate phenyl)phosphine | 4.23 × 10⁻⁴ | 12 | 85 | 2 |
| Comp. Ex. 3 | Diphenyl(5-sodium sulfonate phenyl)phosphine | 4.23 × 10⁻⁴ | " | " | 2 |

| | Reaction Results | | | | |
|---|---|---|---|---|---|
| | Free P/Pd | ΣHOD yield (%) | 1-HOD/ΣHOD (%) | ΣHOD selectivity (%) | TOF |
| Ex. 10 | 4.01 | 59.1 | 94.4 | 87.8 | 700 |
| Comp. Ex. 3 | 0 | 32.8 | 93.8 | 77.8 | 381 |

What is claimed is:

1. A process for producing an alkadienol, which comprises reacting a conjugated alkadiene and water in the presence of carbon dioxide using a palladium compound and a phosphine compound as catalyst, the reaction being carried out with a free phosphine compound present in the reaction solution in an amount of 1 to 150 moles based upon one mole of palladium, the phosphine compound being a tri-arylphosphine compound having at least one aryl group having a substituent at the ortho-position.

2. The process according to claim 1, wherein said phosphine compound is a compound represented by the following formula (I):

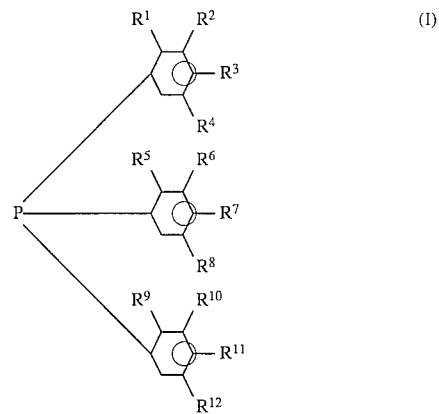

wherein $R^1$, $R^5$ and $R^9$ represent independently a hydrogen or a hydrocarbon group; and $R^2$, $R^3$, $R^4$, $R^6$, $R^7$, $R^8$, $R^{10}$, $R^{11}$ and $R^{12}$ represent independently a hydrogen, an electron donative group or an electron attractive group, but $R^1$, $R^5$ and $R^9$ is not hydrogen, simultaneously.

3. The process according to claim 2, wherein said hydrocarbon group in the formula (I) is an alkyl, an aryl or an alkoxy.

4. The process according to claim 2, wherein the electron donative group in the formula (I) is an alkyl, an alkylamino, an alkoxy, a sulfoalkyl or its salt, an amino, or an alkyl-substituted amino, and the electron attractive group is a sulfo or its salt.

5. The process according to claim 2, wherein in the formula (I), $R^1$, $R^5$ and $R^9$ are the same and represent ($C_1$–$C_4$)alkyl; $R^2$, $R^6$ and $R^{10}$ are the same and represent a hydrogen, a ($C_1$–$C_4$)alkyl, a ($C_1$–$C_4$)alkoxy, a sulfo or a salt thereof, or a sulfo($C_1$–$C_4$)alkyl or a salt thereof; $R^3$, $R^7$ and $R^{11}$ are the same and represent a hydrogen, a ($C_1$–$C_4$)alkyl, a ($C_1$–$C_4$)alkoxy, a sulfo or a salt thereof, or a sulfo($C_1$–$C_4$)alkyl or a salt thereof; and $R^4$, $R^8$ and $R^{12}$ are the same and represent a hydrogen, a ($C_1$–$C_4$)alkyl, a ($C_1$–$C_4$)alkoxy, a sulfo or its salt, a sulfo($C_1$–$C_4$)alkyl or its salt.

6. The process according to claim 1, wherein amount of the free phosphine compound present in the reaction solution is 1.5 to 100 moles based on one mole of palladium.

7. The process according to claim 1, wherein the amount of the free phosphine compound present in the reaction solution is 2 to 100 moles based on one mole of palladium.

8. The process according to claim 1, wherein the conjugated alkadiene is 1,3-butadiene, and the alkadienol is octadienol.

9. The process according to claim 1, wherein the amount of water used is 0.5 to 10 moles based on one mole of conjugated alkadiene.

10. The process according to claim 1, wherein the amount of the palladium compound used is 0.000002 to 1 mole based on one mole of conjugated alkadiene.

11. The process according to claim 1, wherein the amount of the palladium compound used is 0.00002 to 0.1 mole based on one mole of conjugated alkadiene.

12. The process according to claim 1, wherein the amount of the palladium compound used is 0.00002 to 0.0015 mole based on one mole of conjugated alkadiene.

13. The process according to claim 1, wherein the amount of the phosphine compound used is 0.1 to 250 moles based on one mole of palladium.

14. The process according to claim 1, wherein the amount of the phosphine compound used is 3 to 150 moles based on one mole of palladium.

15. The process according to claim 1, wherein the amount of the phosphine compound used is 5 to 150 moles based on one mole of palladium.

16. The process according to claim 1, wherein the reaction is carried out by using a solvent.

17. The process according to claim 16, wherein the solvent is at least one of solvent selected from the group consisting of ethers, ketones, nitriles, aromatic hydrocarbons, alkanes, alkenes, sulfoxides, sulfones, nitro compounds, pyridine derivatives, amines, amides, alcohols and carboxylic acids.

18. The process according to claim 16, wherein the amount of the solvent used is 0.1 to 50 parts by weight based on one part by weight of conjugated alkadiene.

19. The process according to claim 16, wherein the reaction is carried out at room temperature to 180° C.

20. The process according to claim 1, wherein the reaction is carried out under ordinary pressure to 200 kg/cm$^2$.

\* \* \* \* \*